US006620105B2

United States Patent
Sharpe

(10) Patent No.: US 6,620,105 B2
(45) Date of Patent: Sep. 16, 2003

(54) DEVICE FOR ORGANIZING MULTIPLE LEADS

(76) Inventor: Gary L. Sharpe, 21540 Beechwood Rd., Circleville, OH (US) 43113

( * ) Notice: Subject to any disclaimer, the term of this patent is extended or adjusted under 35 U.S.C. 154(b) by 194 days.

(21) Appl. No.: 09/731,187

(22) Filed: Dec. 7, 2000

(65) Prior Publication Data

US 2002/0165457 A1 Nov. 7, 2002

(51) Int. Cl.[7] .................................................. A61B 5/02
(52) U.S. Cl. ...................... 600/508; 600/383; 600/544; 385/137; 385/139; 385/102; 248/68.1; 248/69
(58) Field of Search ................................. 600/383, 544, 600/508; 385/137, 100, 102, 114, 134, 135, 136, 139; 248/68.1, 69, 74.4, 74.2

(56) References Cited

U.S. PATENT DOCUMENTS

| 3,027,419 | A |   | 3/1962  | Owen et al. |         |
|-----------|---|---|---------|-------------|---------|
| 5,144,100 | A |   | 9/1992  | Andel       |         |
| 5,389,082 | A | * | 2/1995  | Baugues et al. | 604/174 |
| 5,566,269 | A | * | 10/1996 | Eberle, Jr. et al. | 385/137 |
| 6,464,181 | B2| * | 10/2002 | Sakakura    | 248/68.1 |

* cited by examiner

Primary Examiner—Teresa Walberg
Assistant Examiner—Shawntina Fuqua
(74) Attorney, Agent, or Firm—Kremblas, Foster, Phillips & Pollick; Patrick P. Phillips

(57) ABSTRACT

A device for organizing multiple leads, with the device having a first component, and a separate second component, with the first and second components being secured together by at least one fastener, and with the device having formed therein a plurality of grooves for the placement therein of leads. The device preferably has an upper surface, a lower surface, two side surfaces, and two ends, with the first and second components being secured together by a pair of fasteners, with one each of the fasteners being located adjacent opposite ends of the device. In one embodiment, the first component has a plurality of apertures formed therein and a plurality of upright wall members, with the wall members forming at least one sidewall in each groove, and the second component has a plurality of integral fasteners, with one each of the fasteners extending through each of the apertures to secure the first and second components together. In this embodiment the second component has a base and a pair of side surfaces each having an interior and an exterior surface, with at least one of the interior surfaces having at least two spaced apart flanges, with the flanges being attached to the base and projecting towards the opposite interior surface. The fastener has serrations and a projection formed thereon. In a second embodiment, the first component has two ends, each terminating in a fastener in the form of a clasp, each clasp engaging the second component and securing said first component to the second component. In the embodiments disclosed, the device is symmetrical about both its length and width.

11 Claims, 6 Drawing Sheets

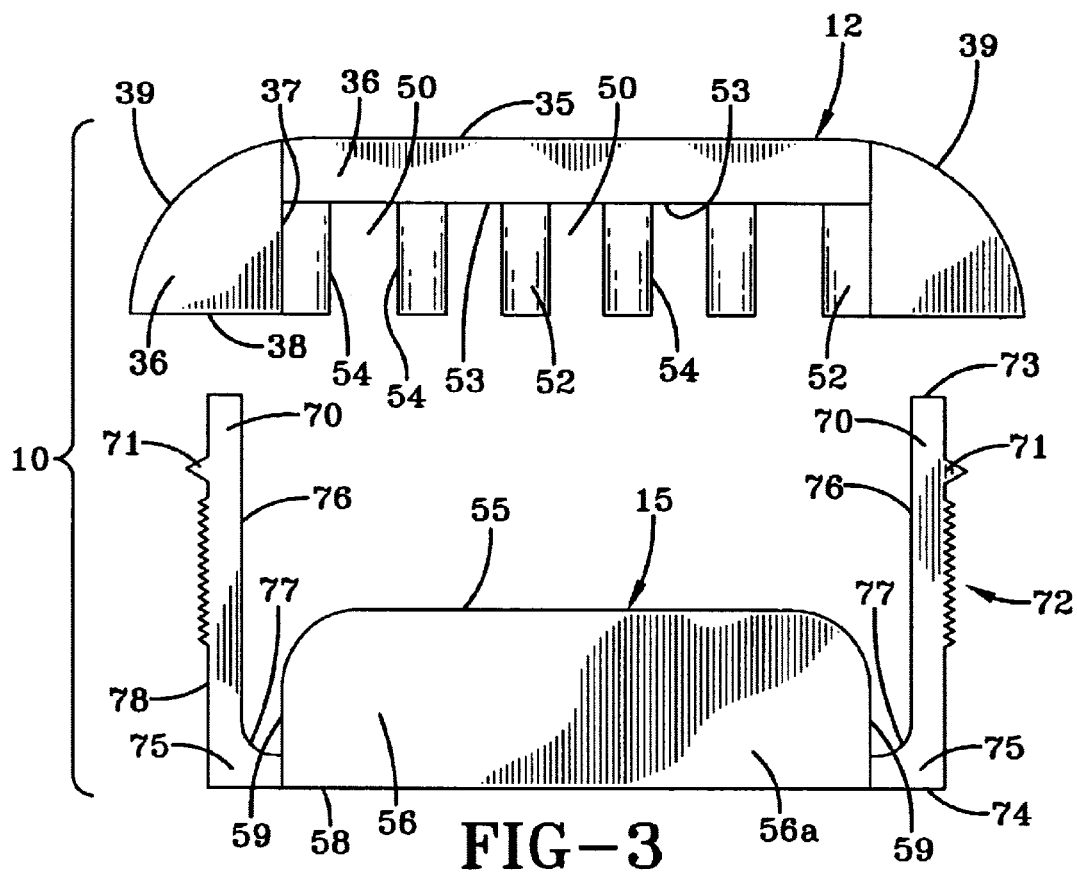
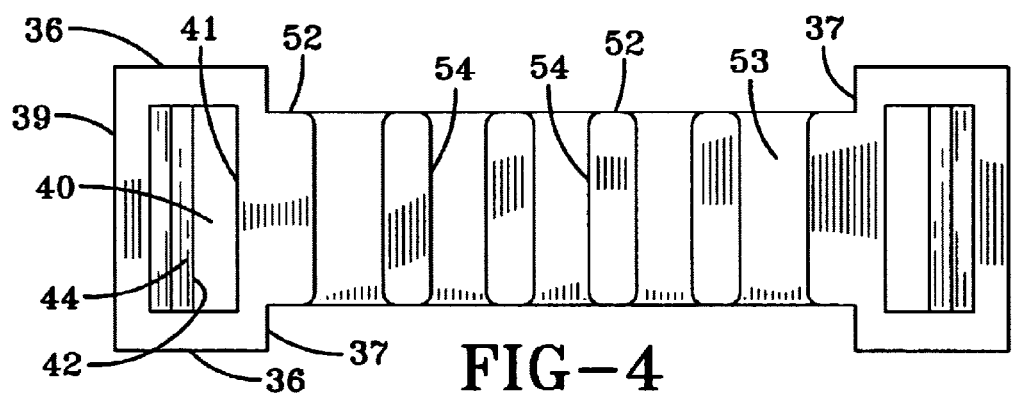
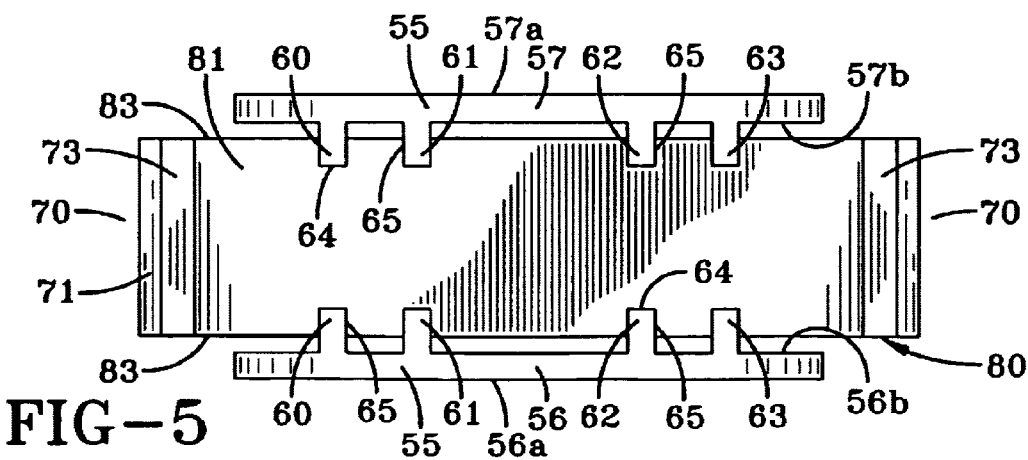

DEVICE FOR ORGANIZING MULTIPLE LEADS

FIELD OF THE INVENTION

This invention concerns a device for organizing multiple leads, and more specifically, one which organizes EEG and EKG leads so as to preclude them from becoming tangled.

BACKGROUND OF THE INVENTION

It is becoming increasingly important in the field of health care for health care professionals to manage their time efficiently. The increasing demands being made on these individuals undoubtedly also have resulted in increased stress. Therefore, it is desirable for tasks to be able to be accomplished in less time, with greater efficiency, and with less stress. Two such tasks concern the administration of electroencephalographs (EEG) and electrocardiographs (EKG). The wires associated with the machines that conduct the aforementioned monitoring have a tendency to become entangled. Thus, either immediately after their use or immediately prior to their next use, a health care professional needs to untwist and straighten out the wires.

Typically, this untwisting and straightening can be accomplished only through the expenditure of considerable time and effort. Many prior efforts to solve the problem have focused on devices that maintain the wires in a separated state through the use of more than one such device spaced a distance apart along the wires. An example of this type of device is disclosed in Owen et al, U.S. Pat. No. 3,027,419, wherein the use of a plurality of harnessing devices is shown. However, this approach potentially requires the use of several such devices. Furthermore, in order to practice the invention, the devices would probably have to stay on the wires, thus necessitating a larger number of such devices be utilized at the monitoring location, since more than one monitoring machine would probably be present. Therefore, attempting to solve the problem with devices like Owen et al could become relatively expensive, and require that the devices be used in a relatively inefficient way.

Another proposed solution to the problem is shown in Andel, U.S. Pat. No. 5,144,100. Three different embodiments of the invention are shown, with each designed to position and align a matrix of wires in an orderly array. In the first embodiment the wires must be inserted into an appropriate aperture and passed through the interior of the device, since there is no lid-type component. To keep the wires from moving once inserted into the device, the second embodiment provides a tether that extends across each of the inserted wires. If the ends of the wires are greater in diameter than the apertures, then the wires can not be placed within the housing. This potential drawback is addressed in the third embodiment by the inclusion of a "J" shaped cover lid. While the manufacturing of the third embodiment of Andel could pose problems relating to cost or ease of manufacture, additionally it should be noted that each of the channels formed in the base of the device are narrowed at their lowermost end for capturing the wire placed therein. Thus, moving the device over the wires in an effort to untangle them after monitoring has occurred apparently was not contemplated by Andel, who arguably wanted the wires in this third embodiment to be in frictional contact with the walls of the channels once the wires were at their desired position relative to the harness.

Thus it can be appreciated that neither patent provides for a single device which can be used with multiple leads to organized them and untangle them by sliding the device over the wires. It is thus apparent that the need exists for an improved device for organizing multiple leads or the like, and more specifically, one which organizes EEG and EKG leads so as to preclude them from becoming tangled.

SUMMARY OF THE INVENTION

The problems associated with organizing multiple leads so as to preclude them from becoming tangled is overcome in accordance with the present invention by forming of a device which organizes leads such as EEG and EKG leads. The device comprises a first component, and a separate second component, with the first and second components being secured together by at least one fastener, and with the device having formed therein a plurality of grooves for the placement therein of leads. The device has an upper surface, a lower surface, two side surfaces, and two ends, with the first and second components being secured together by a pair of fasteners, with one each of the fasteners being located adjacent opposite ends of the device. With respect to certain portions of the device, the first component and second components each have side surfaces that are coplanar.

In one embodiment, the first component has a plurality of apertures formed therein, while the second component has a plurality of integral fasteners, such that one each of the fasteners extending through each of the apertures to secure the first and second components together. The second component comprises a base, a pair of side surfaces each having an interior and an exterior surface, at least one of the interior surfaces having at least two spaced apart flanges, with the flanges being attached to the base, and with the flanges projecting towards the opposite interior surface and with a plurality of integral fasteners attached to the base. Each of the interior surfaces has at least two spaced apart flanges projecting towards the opposite interior surface. The first component has a plurality of upright wall members, with the wall members forming at least one sidewall in each groove, and with the second component having a side surface, with the side surface having an interior surface having at least two spaced apart flanges, each of which flanges are directly adjacent to one of the upright wall members. Additionally, the fastener has serrations and a projection formed thereon.

In a second embodiment of the invention, the first component has two ends, each of the ends terminating in a fastener in the form of a clasp, each clasp engaging the second component and securing the first component to the second component. In this embodiment, the second component has formed thereon a plurality of upright wall members, each of which wall members has a lower wall section and an insert portion. The first component has a bottom surface having formed therein a plurality of apertures, with one of the wall members being inserted into one each of the apertures. The second component has two ends, each of which ends has formed therein a first recessed portion, with the clasp directly adjacent said first recessed portion. Finally, the device is symmetrical about both its length and width.

It is the primary object of the present invention to provide a device for precluding multiple leads from becoming tangled.

A further objective is that such a device be easy and inexpensive to fabricate.

Another objective is that such a device be easy to use.

Other objects and advantages of the invention will be apparent from the following description, the accompanying drawings and the appended claims.

BRIEF DESCRIPTION OF THE DRAWINGS

FIG. 3 is an exploded front elevational view of the device of FIG. 1 in an open position.

FIG. 4 is a bottom plan view of the upper component of the device shown in FIG. 3.

FIG. 5 is a top plan view of the lower component of the device shown in FIG. 3.

DETAILED DESCRIPTION OF THE INVENTION

Figure 1:
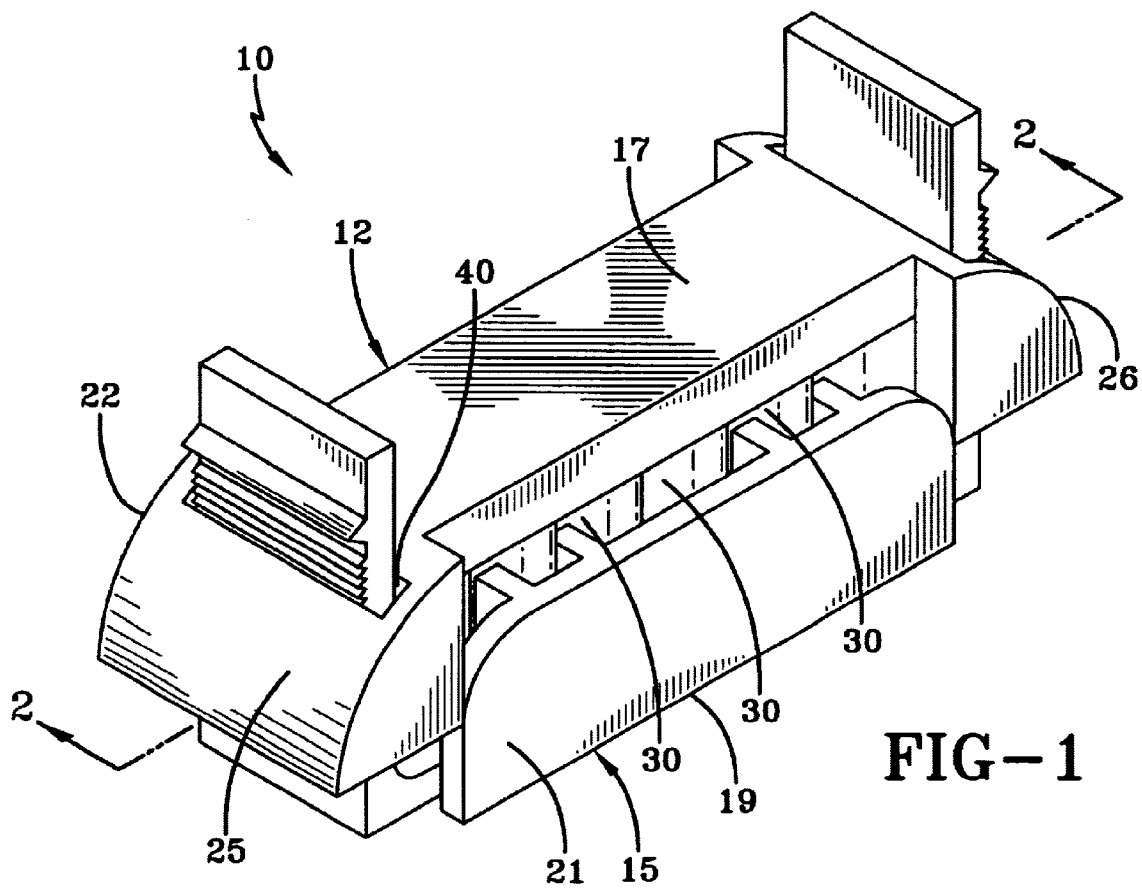
FIG. 1. is a perspective view of a multiple lead organizer made in accordance with the preferred embodiment of the invention.
Figure 2:
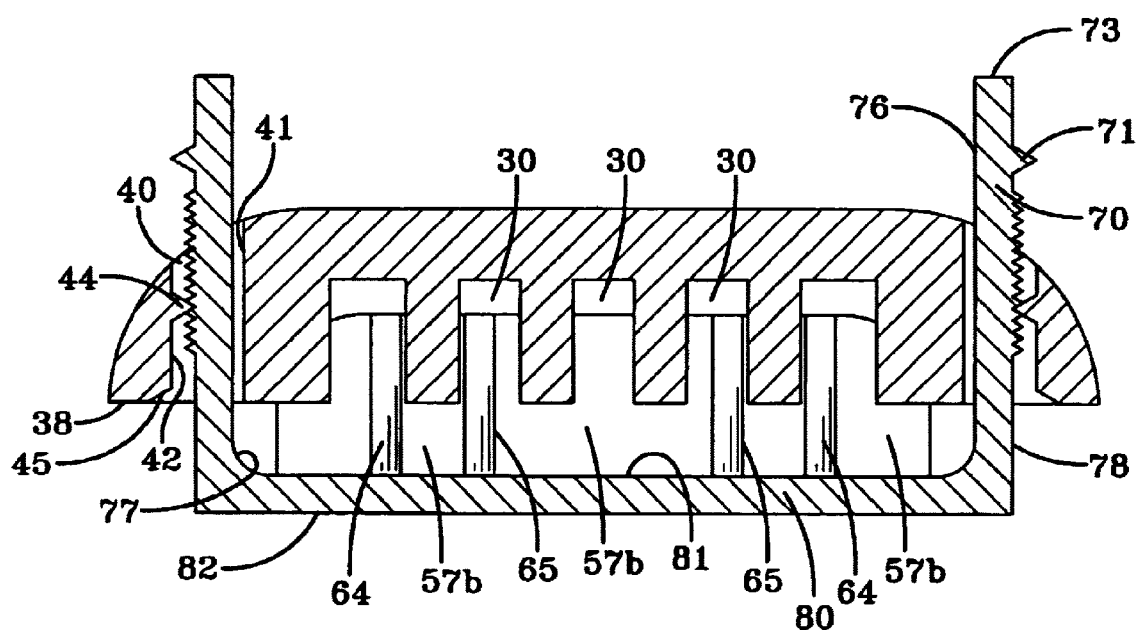
FIG. 2 is a vertical sectional view of the device taken along line 2—2 of FIG. 1.

Having reference to the drawings, attention is first directed to FIG. 1 which discloses a multiple lead organizer made in accordance with this invention and designated generally by the numeral 10. The principal components of this lead identifier and organizer are a first component 12 and a second component 15. The device as shown when assembled has a top surface 17, a bottom surface 19, a pair of side surfaces 21, 22 and ends 25, 26. It will also be appreciated that extending from one side surface 21 to the other are a plurality of apertures 30.

The upper component 12 of the device may be better appreciated from a comparison of FIGS. 1–4. From these drawings, the first component 12 can be seen as having a top surface 35, a pair of side surfaces 36, an inner wall surface 37, a lower surface 38, and ends 39. The top surface 35 is relatively flat and basically parallel to the lower surface 38. The inner wall surface 37 is perpendicular to the side surfaces 36 and extends inwardly beneath the top surface 35. The ends 39 can be appreciated as curving upwardly and inwardly from their lowermost point until reaching top surface 35.

A pair of apertures 40 are formed preferably in the opposite ends of the upper component 12 so as to form a generally vertical channel extending upwardly from the lower surface 38 completely through the first component 12. The interior of that channel is formed such that there is a smooth wall portion 41 and a notched wall portion 42 with a projection 44 having slanted walls which projection extends into the channel. Additionally, it should be noted that at the bottom of the channel there is a recessed wall portion 45 which extends downwardly at an angle from the channel outwardly to the lower surface 38 with this recessed wall portion 45 being at the bottom of the notched wall portion.

The first component 12 also has a plurality of first connector grooves 50 formed therein, with each of the tine-like members extending downwardly from the top surface 17 having groove end walls 52 and groove side walls 54, with the tine-like members being separated by groove top wall 53. The groove end walls 52 may be flat or slightly rounded. Similarly, the groove side walls 54 may be flat or slightly rounded. Similarly, the groove top wall 53 may be flat or slightly rounded. In each instance where a wall section may be slightly rounded, it should be understood that the wall shape would be slightly convex.

Turning now to the second component 15, a comparison of FIGS. 1, 2, 3, and 5 discloses that the lower component 15 has a second connector top surface 55, a second connector side surface 56 and 57, with each of these side surfaces having an exterior side surface 56a and 57a respectively, and interior side surfaces 56b and 57b, respectively. The second component also has a lower surface 58 and a pair of ends 59. Projecting inwardly from at least one side surface and preferably from both are at least two, and preferably more, flanges 60, 61, 62, and 63, each having an inner wall surface 64 and side wall surfaces 65.

At the opposite ends of lower component 15 is at least one and preferably two integral fasteners 70, each of which has a projection 71 extending outwardly therefrom. Additionally, there is a ratchet portion 72 of the fastener 70, with this ratchet portion preferably being below the projection 71. The fastener has a top 73 and a bottom 74, as well as side walls 75. Additionally, there is an inner end wall 76, with a sloped or curved portion 77 near the bottom. Furthermore, the fastener 70 has an outer end wall 78 which is preferably that side or portion of the wall where the ratchet portion is located.

Finally, the second component 15 has a base 80 which extends from one end of the component to the other. The base has a top surface 81 and a lower surface 82, as well as a pair of sides 83. Preferably the base is planar, such that the fasteners 70 project upwardly therefrom. Secured to the base 80 are the lower component flanges 60, which for example in FIG. 5 are shown as being eight in number, although the number could be as few as two provided the flanges project inwardly far enough and are spaced apart a distance such that they cooperate with the wall members comprising the grooves such that one of the groove side walls is directly adjacent one of the lower component flanges.

In actual operation, the integral fastener is inserted into the apertures 40, once the leads have been positioned relative to the grooves. The first and second components are then squeezed together such that the projection 44 passes over the projection 71 and preferably over at least part of the ratchet portion 72, as can be appreciated by reference to FIG. 2. The multiple leads are thus able to be positioned in a separated arrangement in the grooves as shown in aperture 30 of FIG. 1 or FIG. 2.

Figure 6:
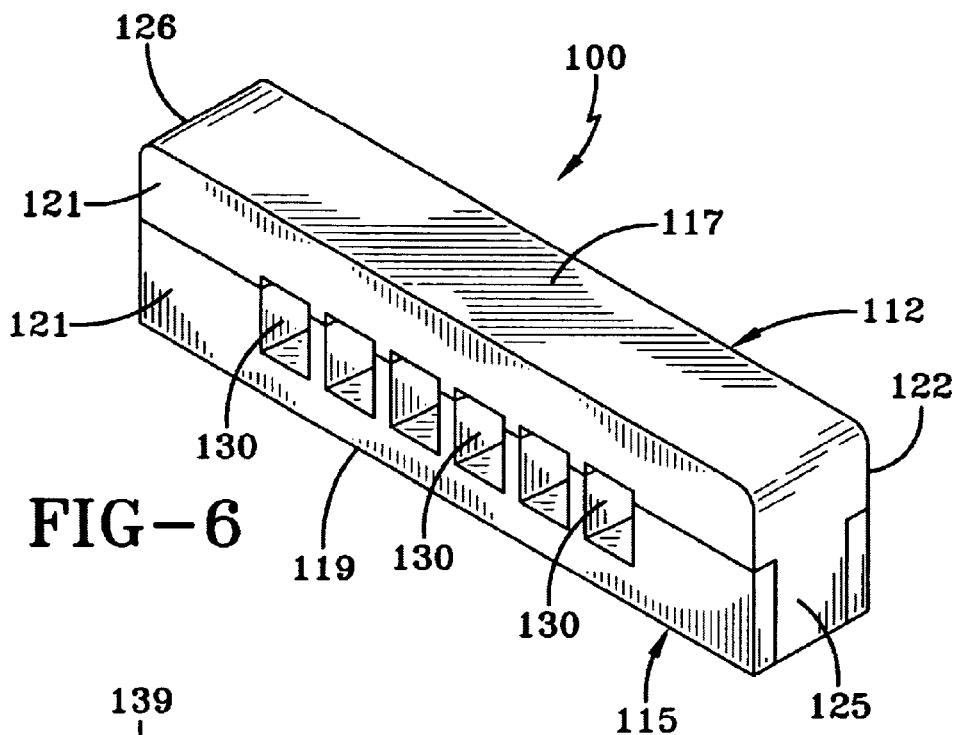
FIG. 6. is a perspective view of a multiple lead organizer made in accordance with a modified embodiment of the invention.

Turning now to the second embodiment of the invention, as shown in FIGS. 6–10, this modified lead identifier and organizer is designated by the numeral 100. This device has a first or upper component 112 and a second or lower component 115 as best shown in FIG. 6. The device has a top surface 117, a bottom surface 119, a pair of side surfaces 121 and 122 respectively, and a pair of ends 125 and 126 respectively, in addition to a plurality of apertures 130.

Figure 7:
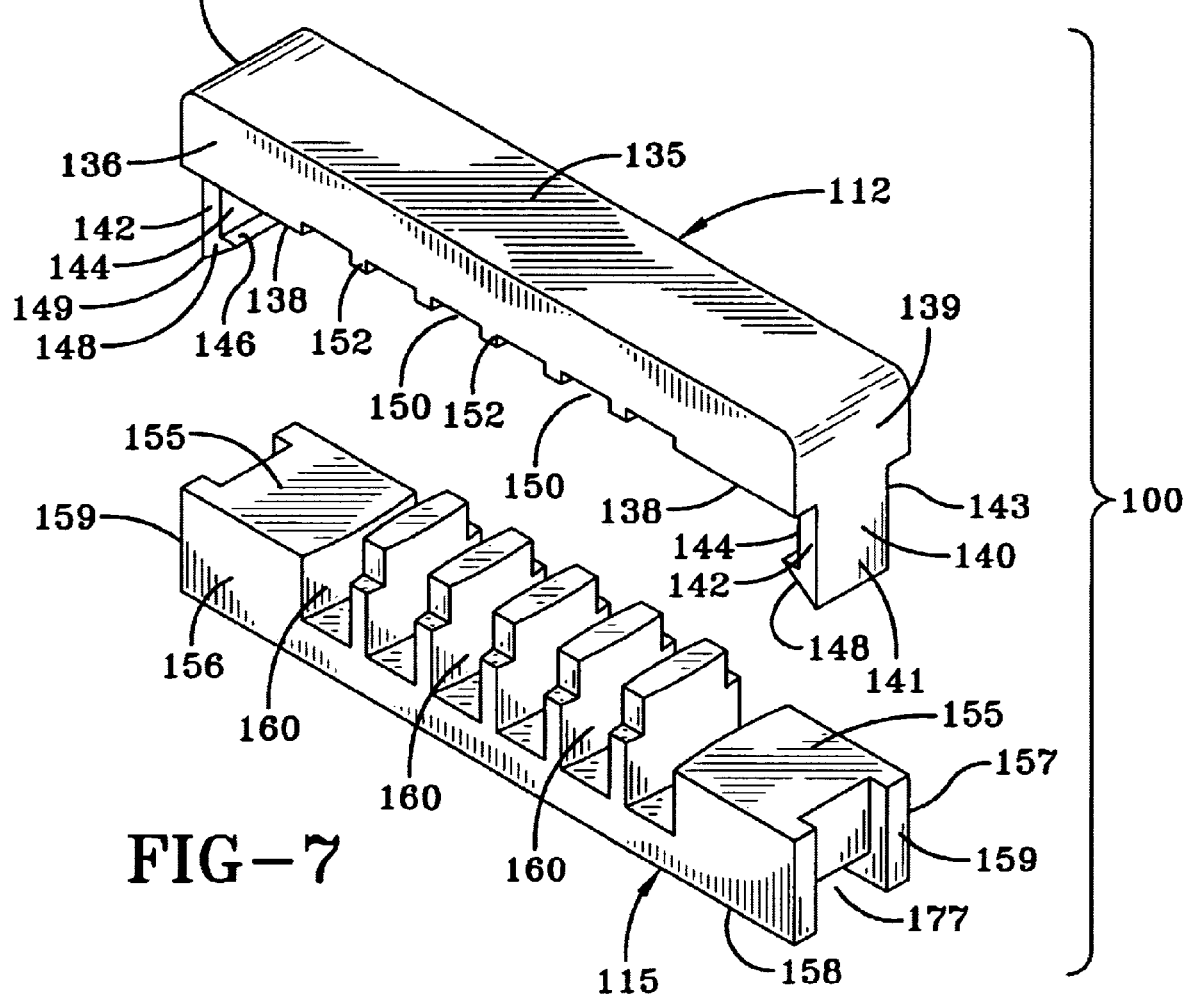
FIG. 7 is an exploded perspective view of the device of FIG. 6.
Figure 8:
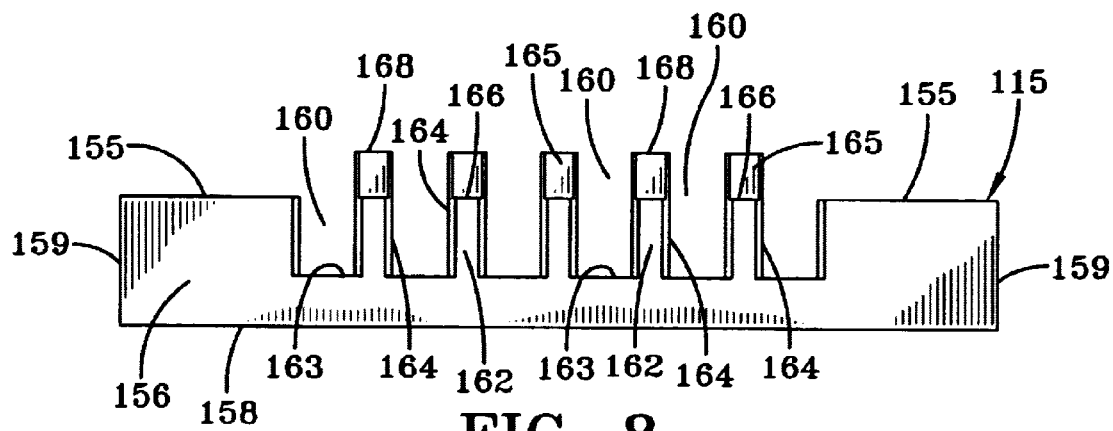
FIG. 8 is a front elevational view of the lower component of the device shown in FIG. 7.
Figure 9:
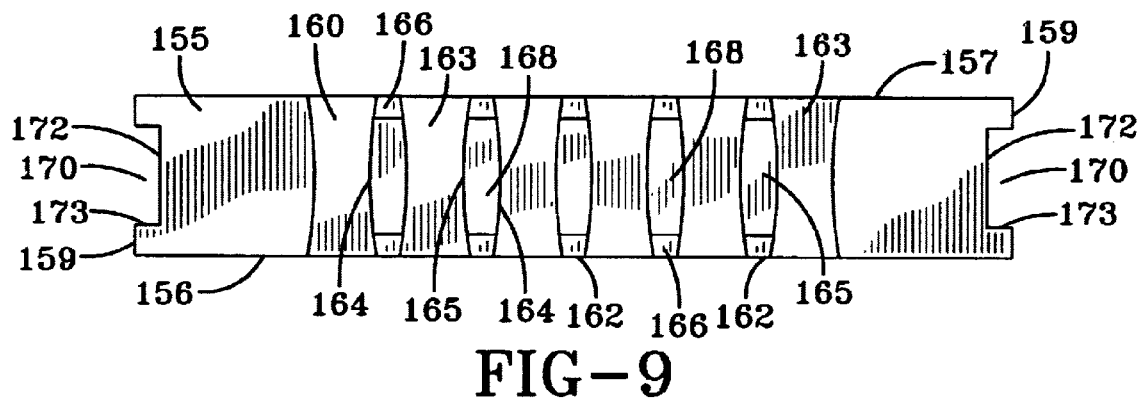
FIG. 9 is a top plan view of the component of the device shown in FIG. 8.
Figure 10:
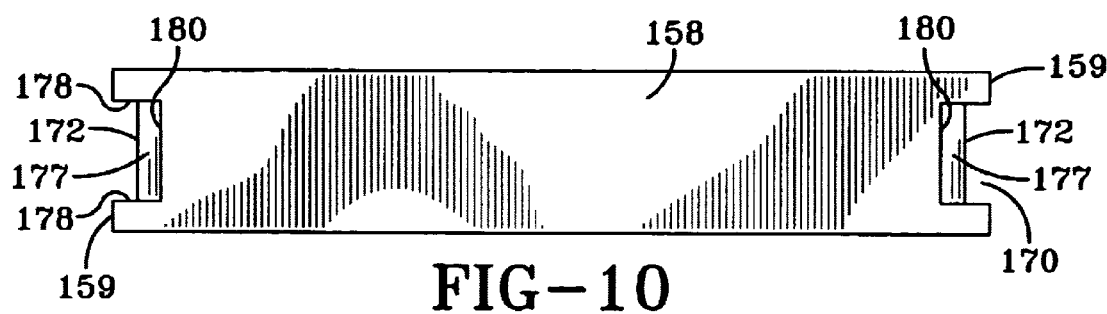
FIG. 10 is a bottom plan view of the component of the device shown in FIG. 8.
Figure 11:
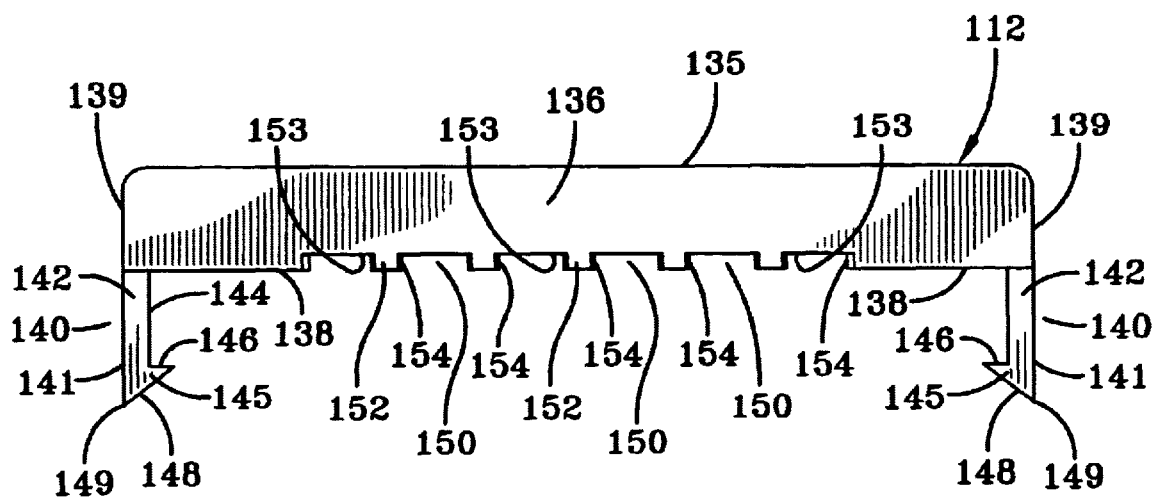
FIG. 11 is a front elevational view of the upper component of the device shown in FIG. 7.
Figure 12:
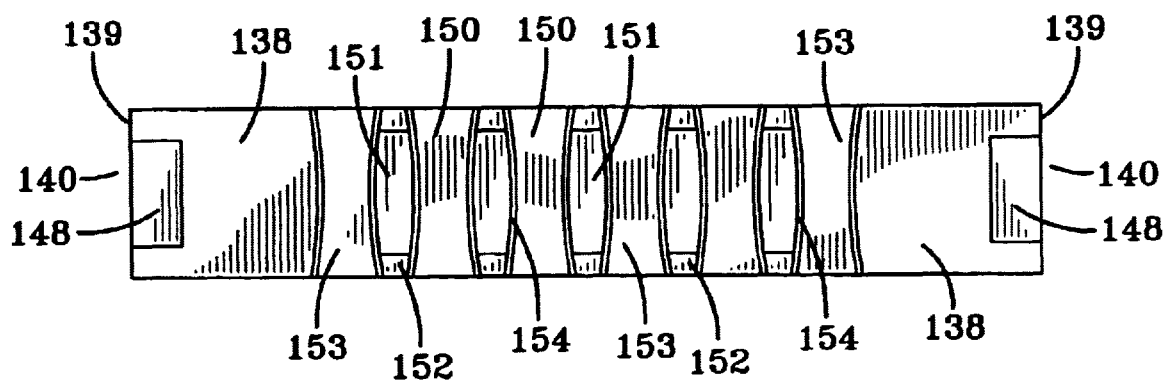
FIG. 12 is a bottom plan view of the component of the device shown in FIG. 11.

The first component 112 may be better appreciated from a comparison of FIGS. 7, 11, and 12, which shows the first component 112 as having a top surface 135 and an upper side surface 137 which is relatively planar and is substantially parallel to the top surface 135. Additionally, there are the two ends 139. Extending downwardly from each of the ends 139 is a clasp member 140 having an outer surface 141, a pair of side surfaces 142, 143, and an inner surface 144. At the bottom of the clasp 140 is a flange member 145 having a top surface 146, and an incline surface 148 which extends downwardly at an angle to the clasp bottom 149.

Across the top of the lower surface 138 are formed a plurality of first component grooves 150 which can be best appreciated from a comparison of FIGS. 7, 11, and 12. Each of these grooves 150 is formed having an insert aperture 151 which extends upwardly into the body of the first component. Additionally, immediately adjacent the insert aperture 151 is an upper wall section 152 which is preferably parallel to the lower surface 138, if not coplanar therewith. Forming the groove 150 are groove top walls 153 and groove side walls 154 all of which are shown as being slightly convex.

The second component 15 has a top surface 155, side surface 156, 157, lower surface 158, and ends 159. Additionally, there are formed in the second component more prominent grooves 160. These grooves have a lower wall section 162, a groove bottom wall 163, and groove side walls 164, both of which are preferably convex although they could be planar. As can be seen by a comparison of FIGS. 7, 8, 9, and 10, the second component also has an insert portion 165 having a lower wall top surface 166 and an insert portion top surface 168. At the opposite ends of lower component 15 are two first recessed portions 170 which are configured so as to accommodate the clasp 140. Each first recessed portion 170 has a central surface portion 172 against which the inner surface of the clasp rests and a pair of first recessed portion side walls 173 which are directly adjacent the side surfaces 142, 143 of clasp 140. At the bottom of each of the ends 159 and extending under the lower component 115 is a second recessed portion 177 which can best be appreciated from a comparison of FIGS. 7 and 10. The dimensions of this second recessed portion are such that the flange 145 can be made to fit within the second recessed portion. The second recessed portion has a pair of side walls 178 and an end wall 180. In actual operation, the leads are placed within the grooves of the second component and the first component is then pressed downwardly such that the clasps 140 slide through the first recessed portions 170 until the flanges engage second recessed portion 177, thereby securing the first and second components to one another.

Figure 13:
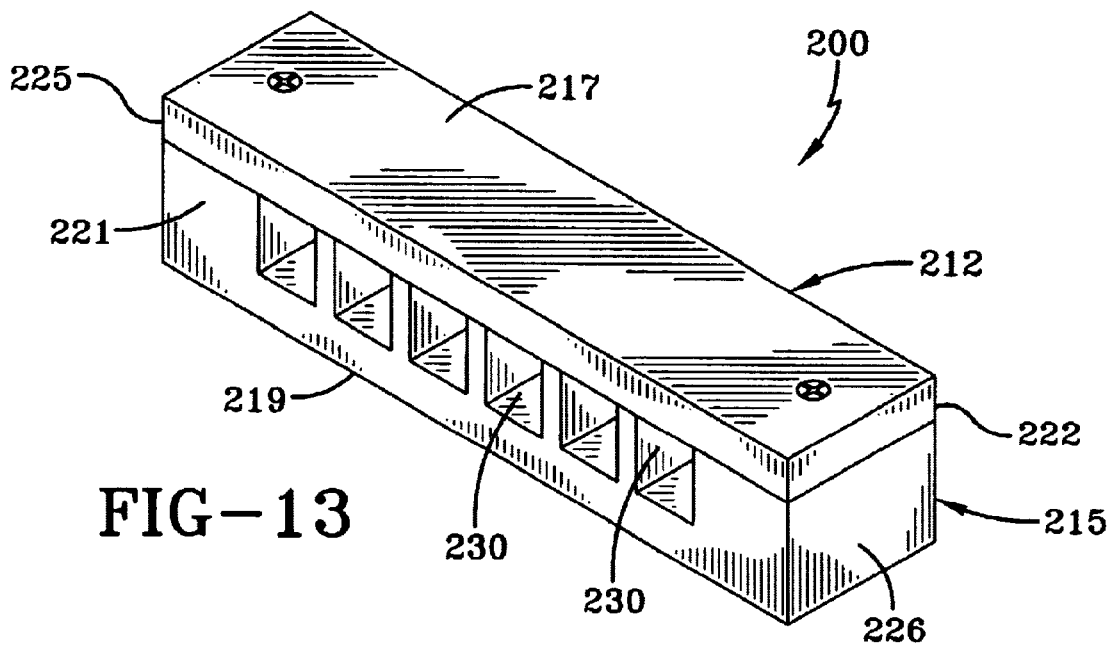
FIG. 13 is a perspective view of a further modified embodiment of a multiple lead organizer.
Figure 14:
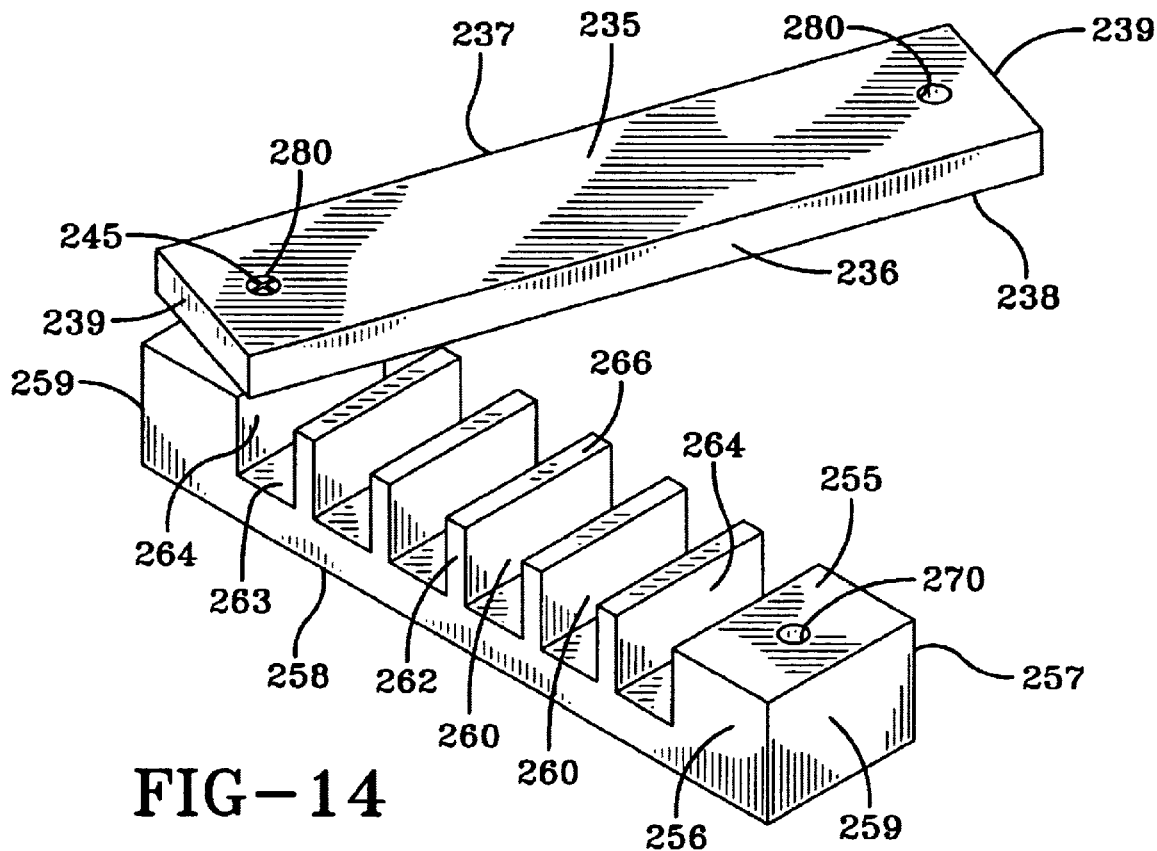
FIG. 14 is a perspective view of the modified embodiment of a multiple lead organizer as shown in FIG. 13, but shown in an open position.

A second modified embodiment of the invention is shown in FIGS. 13 and 14 and designated generally by the numeral 200. The difference between this particular lead organizer and that which is shown in the other two embodiments should be readily apparent. In this modified embodiment, the top is screwed onto the bottom at aperture 240 with fastener 245, instead of being held in place by the clip-like clasp members 140. Once again, the device has a first component 212 and a second component 215. The device has a top surface 217, a bottom surface 219, a pair of side surfaces 221, 222, and ends 225, 226, in addition to a plurality of apertures 230.

While FIG. 13 shows the device intact and as it would appear once the multiple leads are positioned therein, FIG. 14 shows the device open so as to initially receive the leads. From a review of FIG. 14 it may be appreciated that the first component 212 has a top surface 235, upper side surfaces 136, 137, a lower planar surface 138 and an end 139. Additionally, at least one and preferably two, as shown in FIGS. 13 and 14, first component apertures 140 extend completely through the first component from the top to the bottom. Fastener 245 is inserted through the first component aperture 240 into the second component 215 to secure the first and second components together.

The second component 215 may be appreciated as having a top surface 255, a pair of side surfaces 256, 257, a lower surface 258, and ends 259 in to grooves 160. Each of these grooves are formed such that there are a plurality of upright wall sections 262 with each of the grooves then having a groove bottom wall 263 and groove side walls 264. Additionally, each wall section has a top surface 266. Each of the second components are formed having at least one second component aperture 270 into which the fastener 245 is inserted.

In actual use, preferably the components of this device are fabricated from a material such as polystyrene, ABS, or other suitable plastic. Either one or two leads can be positioned in each groove, with the groove dimensions being approximately at least ¼" square. The overall dimension is not critical but probably is somewhere between 2½" to 5" in width, approximately ½" to ¾" deep, and approximately 1" in height. If lead pigtails are used, then one device can be used to separate the two lead pigtails.

The multiple lead organizer associated with this invention precludes the tangling of leads such as those used in applications such as EEG or EKG. The simplicity of the device's construction and operation makes it easy to install the leads in operative relationship thereto. Similarly, the device is easy to use once EEG or EKG monitoring is completed, so that the leads are left untangled ready for their next use. This device eliminates the time consuming unbraiding of tangled lines by the pulling of the device over the lines so as to easily untangle them. This, therefore, saves valuable time by keeping multiple leads organized, thereby preventing line confusion and tangles.

While the form of apparatus herein described constitutes a preferred embodiment of the invention, it is to be understood that the invention is not limited to this precise form of apparatus, and that changes may be made therein without departing from the scope of the invention which is defined in the appended claims.

What is claimed is:

1. A device for organizing multiple leads, said device comprising
   a first component and
   a separate second component, said first and second components being secured together by at least one fastener, said device having an upper surface, a lower surface, two side surfaces, and two ends, with said first and second components being secured together by a pair of fasteners, with one each of said fasteners being located adjacent opposite ends of said device, said device having formed therein a plurality of grooves for the placement therein of leads, said upper surface of said first component having a plurality of apertures formed therein, said second component having a plurality of integral fasteners, one each of said fasteners extending through each of said apertures to secure said first and second components together.

2. The device according to claim 1 wherein said second component comprises a base, a pair of side surfaces extending upwardly from said base each side surface having an interior and an exterior surface, at least one of said interior surfaces having at least two spaced apart flanges, said flanges being attached to said base, said flanges projecting towards the opposite interior surface, and a plurality of integral fasteners attached to said bate.

3. The device according to claim 2 wherein each of said interior surfaces has at least two spaced apart flanges, said flanges projecting towards the opposite interior surface.

4. The device according to claim 1 wherein said first component has an upper surface, a lower surface, two end portions, and a plurality of upright wall members extending perpendicular to said lower surface, said wall members having side surfaces forming at least one sidewall in each groove, said second component having a side surface, said side surface having an interior surface, said interior surface having at least two spaced apart flanges, each of said flanges being directly adjacent to one of said upright wall members.

5. The device according to claim 1 wherein said fastener has serrations and a projection formed thereon.

6. A device for organizing multiple leads, said device comprising
   a first component and
   a second component, said first and second components being secured together by at least one faster, said device having formed therein a plurality of grooves for the placement therein of leads, said first component having two ends, each of said ends terminating in a fastener in the form of a clasp, each clasp having an inwardly facing flange member at the bottom of each clasp, each flange member having a top surface, each of said clasps engaging said end walls of said second component, each of said second component end walls having a recessed portion formed therein, each of said flange members extending into said respective recessed portions second component and securing said first component to said second component.

7. The device according to claim 6 wherein said second component has formed therein a plurality of upright wall members, each of said wall members having a lower wall section and an upper insert portion, said first component has a bottom surface, said bottom surface having formed therein a plurality of apertures, one of said wall members being inserted into one each of said apertures.

8. The device according to claim 1 wherein said first component and second components each have side surfaces that are coplanar.

9. The device according to claim 1 wherein said device is symmetrical about both its length and width.

10. The device according to claim 6 wherein said device is symmetrical about both its length and width.

11. A device for organizing multiple leads, said device comprising
   a first component, and
   a separate second component, said first and second components being secured together by at least one fastener, said device having formed therein a plurality of grooves for the placement therein of leads, said device having an upper surface, a lower surface, two side surfaces, and two ends, with said first and second components being secured together only at said end portions by a pair of fasteners, with one each of said fasteners being located adjacent opposite ends of said device, said second component comprising a base, a pair of end portions, a plurality of upright wall members extending perpendicular to said base towards said first component, said upright members having smooth side surfaces forming at least one sidewall in each groove over which sidewall a lead may easily slide.

* * * * *